(12) United States Patent
Arooni

(10) Patent No.: US 10,321,974 B1
(45) Date of Patent: Jun. 18, 2019

(54) ENDODONTIC FILE

(71) Applicant: Majid Arooni, Chandler, AZ (US)

(72) Inventor: Majid Arooni, Chandler, AZ (US)

( * ) Notice: Subject to any disclaimer, the term of this patent is extended or adjusted under 35 U.S.C. 154(b) by 0 days.

(21) Appl. No.: 15/946,720

(22) Filed: Apr. 5, 2018

(51) Int. Cl.
*A61C 5/42* (2017.01)
*A61C 5/44* (2017.01)

(52) U.S. Cl.
CPC . *A61C 5/42* (2017.02); *A61C 5/44* (2017.02)

(58) Field of Classification Search
CPC ... A61C 5/40–50; A61C 5/80–88; A61C 8/00; A61C 8/0087; A61C 3/02–06; A61C 15/02; A61C 15/045; A61C 19/041–042; A61B 17/06; A61B 17/0064; A61B 2017/06019; A61B 2017/0414; D05B 85/02; A01K 83/00; A01K 91/04
USPC ........... 248/74.1–74.4; D3/28; 223/102, 104; 66/116–118
See application file for complete search history.

(56) References Cited

U.S. PATENT DOCUMENTS

| | | |
|---|---|---|
| 1,619,142 A | 3/1927 | Lippard |
| 2,190,792 A * | 2/1940 | Lippard ................ D05B 85/02 223/102 |
| 2,513,235 A | 6/1950 | Currier |
| 4,321,040 A | 3/1982 | Miller et al. |
| 4,995,536 A * | 2/1991 | Pennestri ............... D05B 85/02 112/222 |
| 5,441,224 A * | 8/1995 | Ludwig .................... F16L 3/22 248/74.2 |
| 6,520,773 B1 * | 2/2003 | Weber ...................... A61C 5/42 433/27 |
| 6,872,075 B2 | 3/2005 | Regan |
| 8,151,720 B2 | 4/2012 | Turner |
| 2009/0035727 A1 | 2/2009 | Maissami |
| 2009/0266281 A1 | 10/2009 | Son |
| 2011/0300506 A1* | 12/2011 | Curry ....................... A61C 5/44 433/75 |

FOREIGN PATENT DOCUMENTS

| | | |
|---|---|---|
| DE | 384457 | * 11/1923 |
| DE | 2925602 | * 1/1981 |
| GB | 240326 | * 11/1924 |

OTHER PUBLICATIONS

Machine Translation of DE 2925602. Accessed on EPO Website on May 29, 2018.*
Machine Translation of DE384457. Accessed at EPO website on Nov. 27, 2018 (Year: 1923).*

* cited by examiner

*Primary Examiner* — Edward Moran
(74) *Attorney, Agent, or Firm* — Thomas W. Galvani, P.C.; Thomas W. Galvani

(57) ABSTRACT

An endodontic file includes a handle and a bore formed entirely through the handle, and a fluted shank extending from the handle along an axis. A notch is formed in communication with the bore, and the notch is configured to open only in a direction along the axis to define an entrance to the bore only in a direction transverse to the axis.

14 Claims, 4 Drawing Sheets

ENDODONTIC FILE

FIELD OF THE INVENTION

The present invention relates generally to dentistry, and more particularly to endodontic tools.

BACKGROUND OF THE INVENTION

When the pulp of a tooth is decayed and unhealthy, endodontic treatment must be administered to prevent further infection. During a root canal procedure, a top portion of the tooth is drilled out to create an access cavity, and a series endodontic files are applied through the tooth. The files are used to bore a hole through the tooth and also to grab and retract infected biomass. In one method of root canal therapy, increasingly-larger files are introduced to the tooth to gradually bore out the hole. Many files are used during a root canal.

Endodontic files are quite small. They are usually less than 5 centimeters long and their handles are only a few millimeters in diameter. They can be difficult to manipulate and are quite easy to drop. When dropped, because of their small size and the prone position of the patient, the files can be swallowed and may even pierce the throat or lung. Emergency medical attention is usually required when a file is dropped and the patient inadvertently swallows it.

Many files have small bores near their tops through which dentists can thread floss. In the event that a file is dropped, the dentist can pull the floss up and pull the file out of the patient's throat. However, bores are small and difficult to thread with floss. Further, the dentist and any assistants in the procedure wear protective gloves, usually covered in the patient's saliva. The lack of dexterity makes threading the floss through the bore even more difficult. As such, many dentists choose not to attach floss to the file, and instead place the patient's health at jeopardy.

SUMMARY OF THE INVENTION

An endodontic file includes a handle and a bore formed entirely through the handle, and a fluted shank extending from the handle along an axis. A notch is formed in communication with the bore, and the notch is configured to open only in a direction along the axis to define an entrance to the bore only in a direction transverse to the axis. A length of floss can be pulled through the notch and into the bore for capture and retention therein. This is an easy way to apply floss to the endodontic file.

The above provides the reader with a very brief summary of some embodiments discussed below. Simplifications and omissions are made, and the summary is not intended to limit or define in any way the scope of the invention or key aspects thereof. Rather, this brief summary merely introduces the reader to some aspects of the invention in preparation for the detailed description that follows.

BRIEF DESCRIPTION OF THE DRAWINGS

Referring to the drawings.

DETAILED DESCRIPTION

Figure 1:
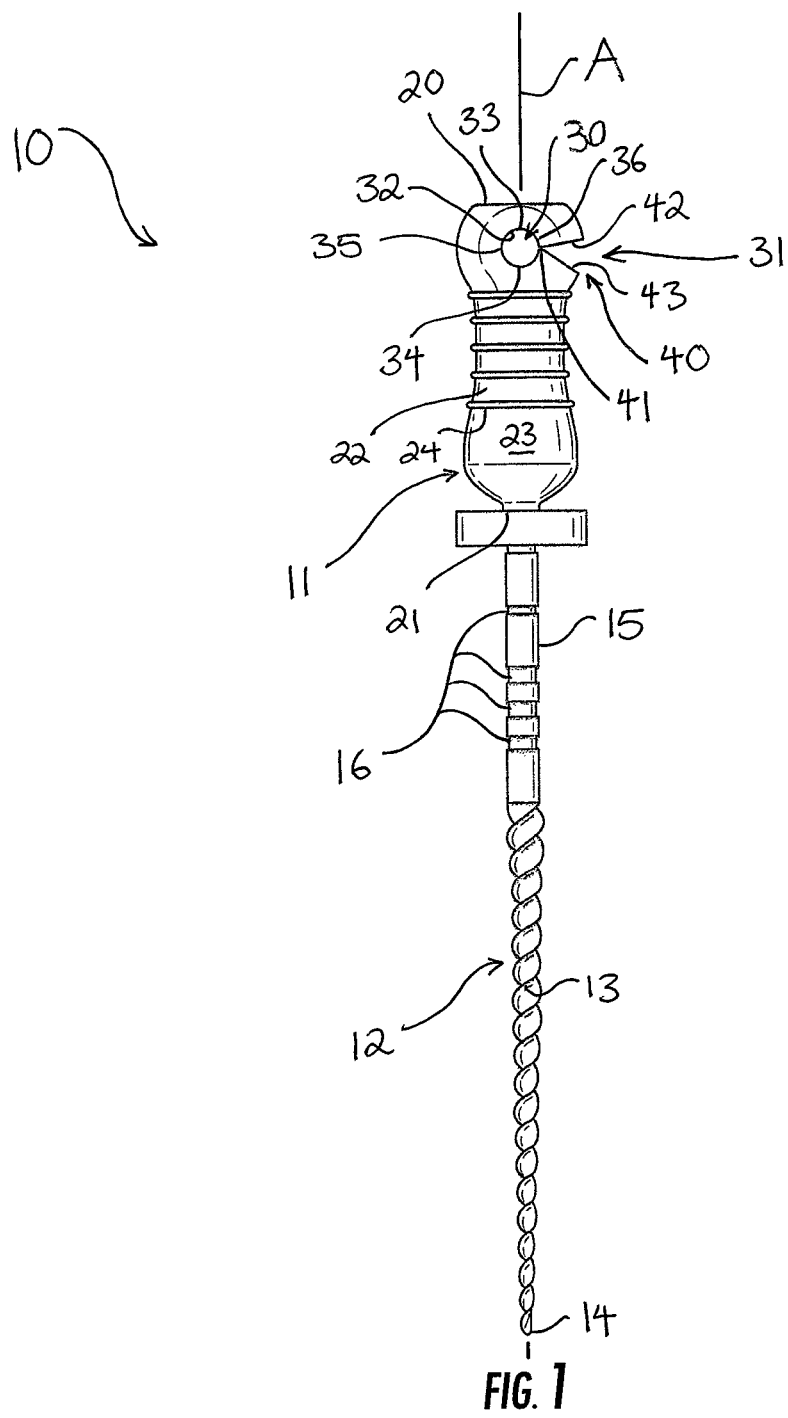
FIG. 1 is a side elevation of an endodontic file.

Reference now is made to the drawings, in which the same reference characters are used throughout the different figures to designate the same elements. FIG. 1 is a side elevation showing an endodontic file 10. The file 10 has a handle 11 and a shank 12 extending from the handle 11 along an axis A. The shank 12 is fluted; it is formed with a cutting edge 13 wrapping helically toward a tip 14 of the shank 12. An upper portion 15 of the shank 12 is not fluted and is instead smooth but for annular channeled indicators 16 for determining the bore depth of the file 10 when in use. The indicators 16 may be coded with different colors.

The handle 11 has a top 20 and an opposed bottom 21, with a generally cylindrical body 22 defined therebetween. In the embodiment shown in FIG. 1, the body 22 is slightly bulbous proximate the top 20 and bottom 21, but generally, the body 22 has a cylindrical shape. An outer surface 23 of the body 22 is smooth but for a plurality of vertically spaced-part ribs 24 between the bulbous top 20 and bottom 21. One having ordinary skill in the art will readily appreciate that in other embodiments, the body 22 may have other shapes and may or may not have ribs or the same rib configuration. FIG. 1 merely shows an exemplary configuration of the body 22.

The handle 11 has rotational symmetry about the axis A but for a bore 30 and notch 31. The bore 30 is a cylindrical hole having two open ends, formed entirely through the handle 11, and suitable for receiving and capturing a length of floss therein. The bore 30 is bound by an inner wall 32 which has a cylindrical shape thereby defining the cylindrical shape of the bore 30. The inner wall 32 is continuous but for the notch 31, which will be described later. By continuous, it is meant that the cylindrical shape is maintained entirely around the bore 30 and the inner wall 32 without any projections, depressions, recesses, or other incongruities into or out of the bore 30. The inner wall 32 is smooth. A length of floss within the bore 30, when pulled around the bore 30 against the inner wall 32, does not catch on any feature but instead slides smoothly along the inner wall 32.

The inner wall 32 of the bore 30 has a top 33 and an opposed bottom 34. The top 33 is directed toward the top 20 of the handle 11, and the bottom 34 is directed toward the bottom 21 of the handle 11. The bore 30 includes opposed open ends, one of which is shown in FIG. 1. Further, the inner wall 32 around the bore 30 includes opposed lateral sides 35 and 36. The word "lateral," as it is used in this specification, means extending outward from the axis along a direction normal or substantially to the axis A. The top 33, bottom 34, and side 35 are all unbroken and uninterrupted by the notch 31, and are integral and monolithic. The side 36, however, is severed by the notch 31, forming a continuous and contiguous, but not uninterrupted, portion of the inner wall 32.

The top 33, bottom 34, side 35, and severed side 36 are nonetheless formed integrally within the body 22 of the handle 11. The body 22 around the bore 30 is relatively thick when compared with the bore 30 itself; the body 22 has a width approximately three times greater than the diameter of the bore 30. In other words, the structure surrounding the bore 30 is just as thick or wide as the bore 30. The top 33, bottom 34, side 35, and severed side 36 thus have great rigidity, resiliency, and strength, and are generally lacking in flexibility. Minimal flexibility assists in preventing a length of floss from being pulled out of the bore 30 through the notch 31.

Still referring to FIG. 1, the construction of the notch 31 itself also mitigates the risk that the floss will come loose. The notch 31 is wedge-shaped: it has a wide opening 40 at the outside of the handle 11 which narrows to an inner end 41 terminating at the inner wall 32, thereby extending laterally through the handle 11 to the bore 30. The notch 31 includes flat a first or upper face 42 and an opposed, flat and convergent second or lower face 43 each extending inwardly into the handle 11.

The upper and lower faces 42 and 43 converge into each other toward the bore 30. While the upper and lower faces 42 and 43 are spaced apart from each other at the opening 40, they meet and touch at the inner end 41. At the opening 40, the upper and lower faces 42 and 43 are separated by a distance equivalent to the diameter of the bore 30. At the inner end 41, the upper and lower faces 42 and 43 are in contact with each other, but can be separated from each other to provide access to the bore 30. As such, the notch 31 is in communication with the bore 30 to move small objects, such as a length of floss, from the notch 31 into the bore 30.

Moreover, the wedge-shaped design of the notch 31 guides small objects toward the inner end 41 and into the bore 30 for capture by the bore 30. When a length of floss is near the opening 40 of the notch 31 and is pulled toward the bore 30, the floss will be pulled along either the upper face 42 or the lower face 43 until it is brought to the inner end 41, at which point it can be pulled forcefully into the bore 30.

Figure 2B:
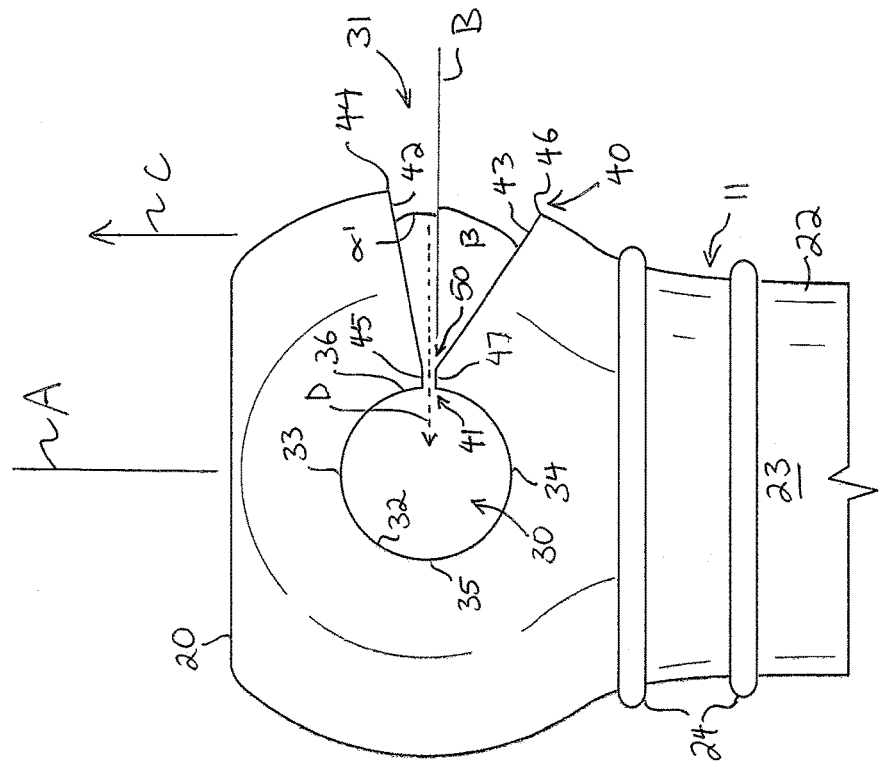
FIGS. 2A and 2B are enlarged views showing closed and open conditions of a notch in the endodontic file, respectively.
Figure 2A:
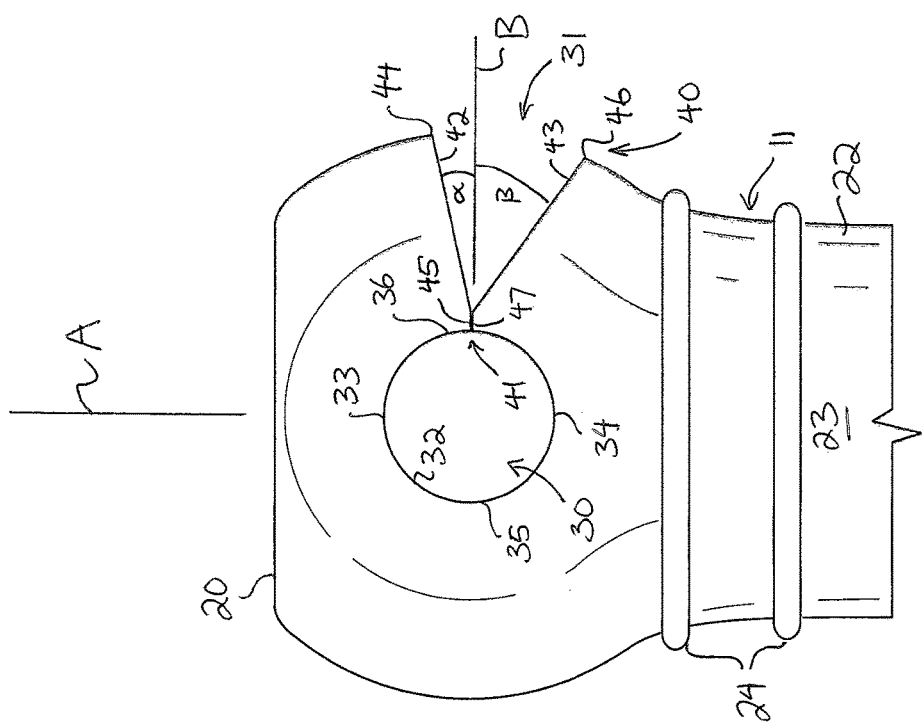

Referring now to FIGS. 2A and 2B, which show the handle 11 in greater detail, the construction of the bore 30 and the notch 31 can be seen clearly. The outer surface 23 of the body 22 proximate to the notch 31 is curved: just above the notch 31, the outer surface 23 is arcuate and curves downward from the top 20 at a constant radius from the bore 30 until the outer surface 23 meets the upper face 42 at an upper edge 44. From the upper edge 44, the upper face 42 extends inwardly and downwardly toward the bore 30 to an upper rear edge 45 at the inner end 41. Similarly, the outer surface 23 of the body 22 proximate to the notch 31 just below the notch 31 is arcuate and curves upward at a constant radius from the bore 30 until the outer surface 23 meets the lower face 43 at a lower edge 46. From the lower edge 46, the lower face 43 extends inwardly and upwardly toward the bore 30 to a lower rear edge 47 at the inner end 41. The first and second faces are longer than the upper and lower rear edges as shown in FIGS. 2a-b.

A line B is shown in both FIGS. 2A and 2B. The line B extends normal to the axis A. The notch 31 is not symmetric with respect to this line B, and the upper and lower faces 42 and 43 are similarly not symmetric with respect to the line B. The upper face 42 defines an angle $\alpha$ with the line B, and the lower face 43 defines an angle $\beta$ with the line B. The angle $\alpha$ is smaller than the angle $\beta$, so that the lower face 43 drops below the line B more so than does the upper face 42 rise above the line B. This assists in placement of the length of floss into the notch 31, as is described later.

The upper and lower edges 44 and 46 are separated by the opening 40 and never come into contact with each other unless the endodontic file 10 suffers catastrophic damage. The upper rear edge 45 and the lower rear edge 47 are alternately arranged in contact and separation. FIGS. 2A and 2B show the notch 31 of the endodontic file 10 in a first or closed condition and a second or open condition, respectively.

In the closed condition of the notch 31 shown in FIG. 2A, the upper rear edge 45 is in flush and direct contact with the lower rear edge 47. This closed condition defines an at-rest state for the endodontic file 10; the file 10 is in this condition when no floss is being actively pulled into the bore 30 and in other situations, as will be explained. In the closed condition, the upper rear edge 45 and the lower rear edge 47 define the inner end 41 of the notch 31 as a smooth feature, contiguous to the severed side 36 and thereby maintaining the continuous cylindrical shape of the inner wall 32 bounding the bore 30. From inside the bore 30, the inner end 41 presents no interruption to the smooth inner wall 32, and so is not a feature on which floss could be caught or snagged. Rather, floss slides smoothly over the inner end 41 as it moves or is pulled around the inner wall 32.

In the open condition of the notch 31, the upper rear edge 45 is separated from the lower rear edge 47 by a gap 50 created when the upper and lower rear edges 45 and 46 move apart in response to the notch 31 opening in a direction along the axis A, as indicated by the arrowed line C in FIG. 2B. In this open condition, the upper rear edge 45 and the lower rear edge 47 now define the inner end 41 as a discontinuity in the inner wall 32, or as an interruption in the otherwise smooth and continuous inner wall 32. When the notch 31 is moved into the open condition, a small object such as a length of floss can be pulled through the notch 31, through the gap 50 at the inner end 41 of the notch 31, and into the bore 30. When the notch 31 opens in the direction along line C, the notch 31 defines a path or entrance D into the bore 30, as indicated in broken line in FIG. 2B. The entrance D extends only in a direction transverse to the axis A, as shown in the drawing. This direction is oriented along a line bisecting the angle between the upper and lower faces 42 and 43. In other words, the entrance D is a path equidistant between the upper and lower faces 42 and 43. Floss moving through the notch 31 into the bore 30 generally follows this entrance D.

When the notch 31 is moved into the open condition thereof, the angle $\alpha$ is enlarged slightly. Because the upper face 42 moves slightly upward along the direction of the line X, the upper face 42 defines a new angle $\alpha'$ with the line B. The angle $\alpha'$ is slightly larger than the angle $\alpha$. This new angle $\alpha'$ is still smaller than the angle $\beta$, which has the same magnitude in both the closed and open conditions of the notch 31.

Figure 3:
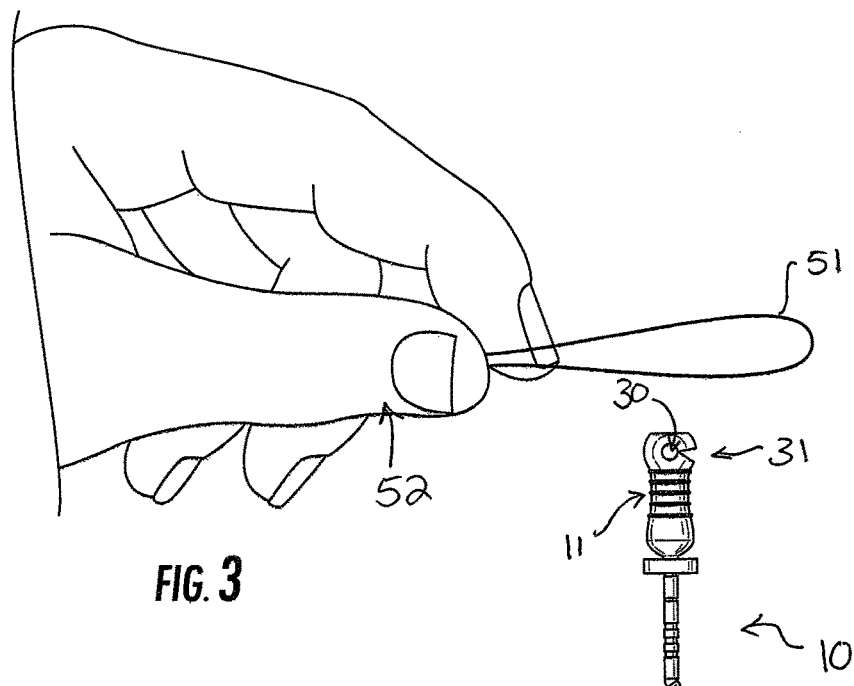
FIGS. 3-6 are side elevations of the endodontic file being applied with a length of floss and made ready for use.

Turning now to FIGS. 3-6, the drawings show a sequence of steps of applying a length of floss 51 to the endodontic file 10 for capture by and retention in the bore 30. While the bore 30 can of course still be directly threaded by inserting a free end of the floss 51 into one of the open ends of the bore 30, the below method is a faster, easier, and more reliable method of capturing the floss 51 within the bore 30. The length of floss 51 is preferably initially formed into a loop, as shown in FIG. 3, which eases application into the bore 30.

Figure 4:
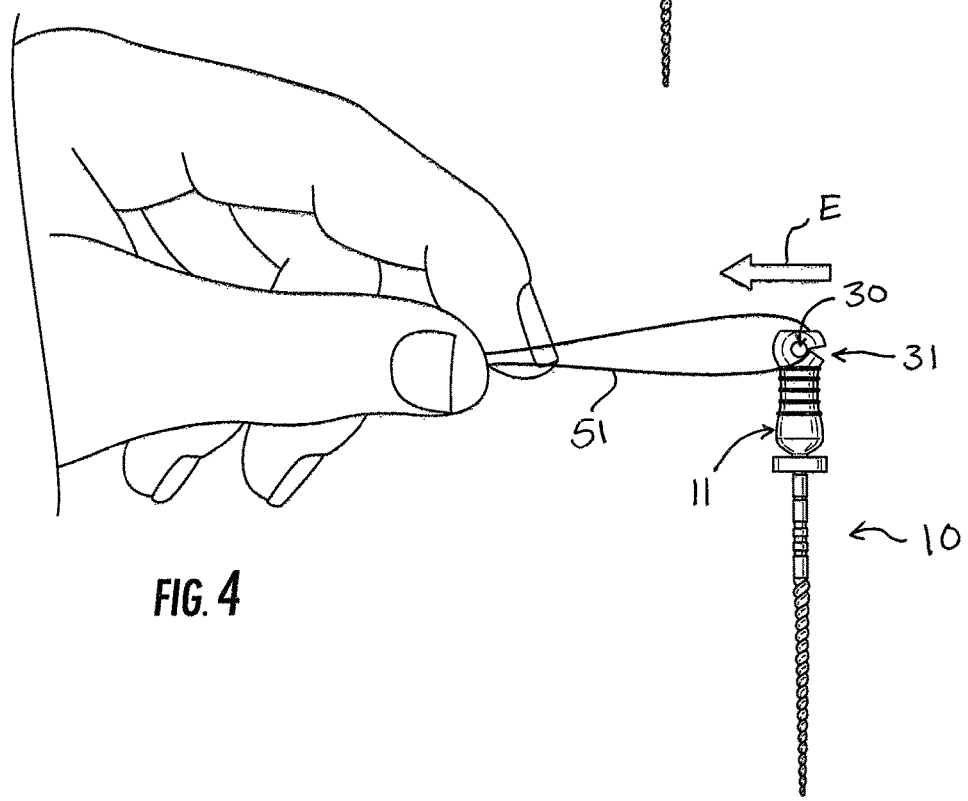

The loop of floss 51 is taken up by hand 52 and brought close to the handle 11 of the endodontic file 10, as shown in FIG. 3. The loop of floss 51 is then placed into the notch 31, as shown in FIG. 4. The floss 51 can be introduced into the notch 31 in a few ways. In a first manner, the floss 51 can be pulled directly into the opening 40 (Briefly, the reference character 40 is shown in FIGS. 1, 2A, and 2B but not in FIGS. 3-6. Indeed, many of the reference characters are not used in FIGS. 3-6 for simplicity of the drawings, but are instead shown in the prior drawings). When pulled directly into the opening 40, the loop of floss 51 is registered just outside of the opening 40 and then pulled directly in. The floss 51 may contact the upper or lower faces 42 and 43, but generally, the floss 51 is drawn directly toward the inner end 41 of the notch 31.

In another manner, the endodontic file 10 is gripped in one hand, and the loop of floss 51 is registered with the handle 11 between the notch 31 and the bottom 21 of the handle 11. The floss 51 is then pulled upward and toward the handle 11, so as to draw it upward. This causes the floss 51 to ride along the outer surface 23 of the handle 11 until it crests the lower edge 46, at which point the floss 51 passes through the opening 40 and into the notch 31, sliding along the lower face 43 toward the inner end 41 of the notch 31. The angle β allows the floss 51 to quickly and smoothly slide toward the inner end 41.

In yet another manner, the endodontic file 10 is gripped in one hand, and the loop of floss 51 is registered with the handle 11 between the notch 31 and the top 20 of the handle 11. The floss 51 is then pulled downward and toward the handle 11, so as to draw it downward. This causes the floss 51 to ride along the outer surface 23 of the handle 11 until it crests the upper edge 44, at which point the floss 51 passes through the opening 40 and into the notch 31, sliding along the upper face 42 toward the inner end 41 of the notch 31.

Regardless of the manner used to introduce the floss 51 into the notch 31, the floss 51 is eventually brought into confrontation with the upper rear edge 45 and the lower rear edge 47. The notch 31 is in the closed condition, and as such, the upper rear edge 45 and the lower rear edge 47 are in flush and direct contact with each other. The floss 51 cannot be advanced into the bore 30 without a greater application of force. And so, the dental worker pulls on the loop of floss 51 in the direction of the arrowed line E in FIG. 4.

Figure 5:
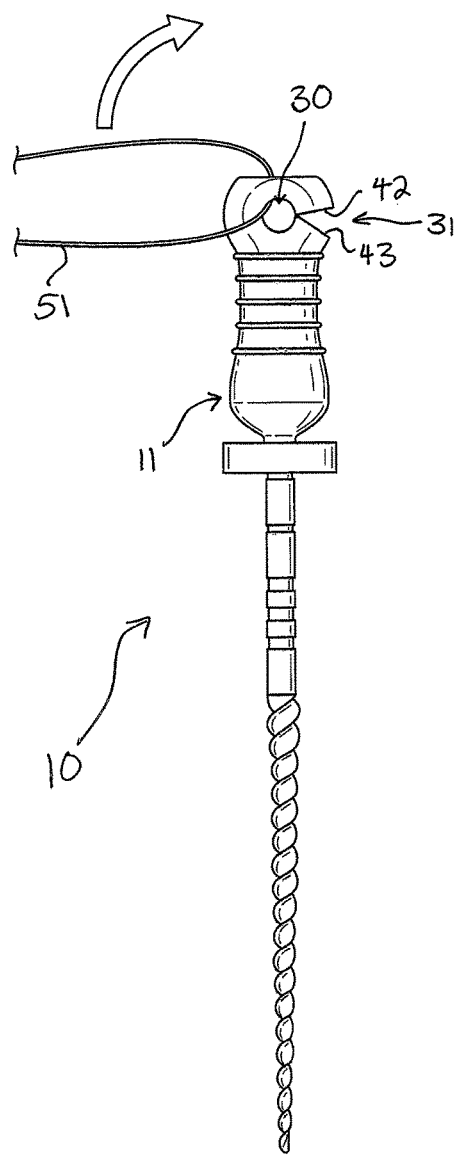
Figure 6:
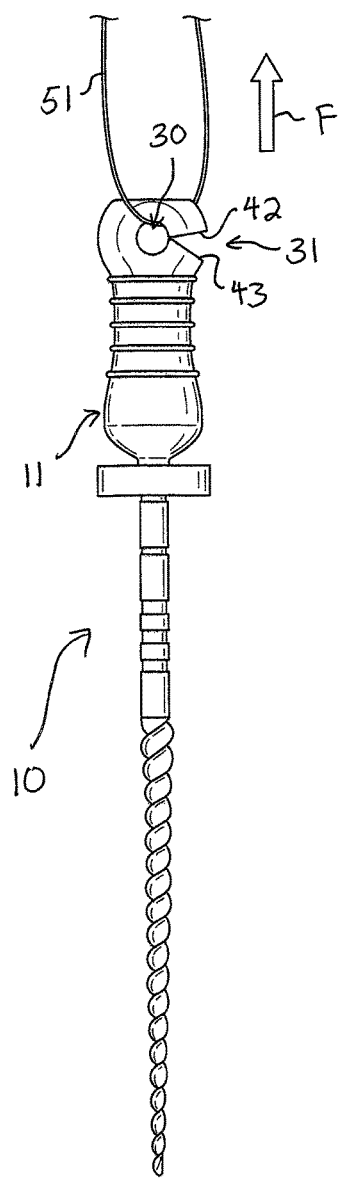

Because the upper and lower faces 42 and 43 converge into each other, and converge into each other about the entrance D, and the direction of applied force along line E is substantially oriented parallel to the entrance D, the force is applied to the floss 51 and the floss 51 in turn exerts an opening force on the upper and lower faces 42 and 43. This opening force is directed outward, against the upper and lower faces 42 and 43. The top 33, bottom 34, and side 35 of the inner wall 32 are integral and monolithic and as such do not yield to the force. The lower face 43 does not move, but the upper face 42 moves upward slightly, only in the direction of the line C, along the axis A. The lower face 43 does not move inward or outward transverse to the axis A, and so the notch 31 opens only in the direction of the line C. This upward movement of the lower face 43 places the notch 31 in the open condition thereof and creates the gap 50 through which the floss 51 can slip into the bore 30, as shown in FIG. 5.

Once the floss 51 slips past the gap 50, the notch 31 immediately closes, biased by the resiliency of the handle, thereby returning the notch 31 to the closed condition thereof. The floss 51 is retained in the bore 30 and can ride smoothly around the entire, continuous, cylindrical inner wall 32. Any pulling force on the floss 51 applied at the inner end 41 will not tend to open the notch 31, because the force is directed radially outward. Since the inner wall 32 is cylindrical, a radially-outward-directed force urges the inner wall 32 to move laterally, which it does not do because of the rigidity of the handle 11. Such a force does not tend to move the upper and lower faces 42 and 43 apart from each other so as to create a gap 30. In other words, only pulling the floss 51 from the outside in through the notch 31 moves the notch to the open condition; pulling the floss 51 from the bore out does not.

The endodontic file 10 is now ready for use. The dentist can use the endodontic file 10 in a procedure, and if the file 10 is dropped, the dentist pulls on the floss 51 in the direction F shown in FIG. 6. This will retract the file 10 upwardly, with the tip 14 of the file 10 directed downwardly, minimizing the risk of further harm.

The retraction force F is applied to the endodontic file 10 at the top 33 of the bore 30 and is oriented along the axis A. The notch 31 extends laterally into the bore 30, circumferentially offset from the location at which the force F is being applied. There is thus no risk that the floss 51 will be pulled out through the notch 31 of the handle 11 when the dentist retracts the endodontic file 10 from the patient's mouth or throat. Further, because the inner wall 32 is smooth and uninterrupted, there is no risk that the floss 51 will catch on the inner end 41 of the notch 31, open it, and be pulled through the notch 31.

A preferred embodiment is fully and clearly described above so as to enable one having skill in the art to understand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

The invention claimed is:

1. An endodontic file comprising:
   a handle and a bore formed entirely through the handle, the bore bound by an inner wall;
   a fluted shank extending from the handle along an axis, wherein the bore is aligned transverse to the axis;
   a notch formed in communication with the bore, and defining an entrance to the bore only in a direction transverse to the axis, the notch comprising opposed, flat, and convergent first and second faces extending and converging inwardly into the handle and terminating at opposed, flat, and parallel upper and lower rear edges, respectively, at an inner end of the notch at the inner wall, wherein the notch is biased to move from an open condition of the notch to a closed condition of the notch;
   the first and second faces are longer than the upper and lower rear edges;
   the first face is oriented downward and inward at a first angle with respect to a line extending through the notch normal to the axis, and the second face is oriented upward and inward at a second angle with respect to the line extending through the notch normal to the axis, and the second angle is greater than the first angle;
   in the closed condition of the notch, the first and second faces are separated from each other, and the upper and lower rear edges are in flush and direct contact, so that the inner end of the notch maintains continuity of the inner wall of the bore;
   in the open condition of the notch; the first and second faces are separated from each other, and the upper and lower rear edges are separated from each other by a gap, so that the inner end is a discontinuity in the inner wall of the bore; and
   during movement of the notch between the open and closed conditions, the first and second faces move toward and apart from each other in a direction aligned with the axis.

2. The endodontic file of claim 1, wherein the notch extends through the handle to the bore in a direction which is lateral to the axis.

3. The endodontic file of claim 1, wherein the bore has a cylindrical shape.

4. The endodontic file of claim 1, wherein the first and second faces are asymmetric with respect to the line extending normal to the axis.

5. The endodontic file of claim 1, wherein the bore has a closed top unbroken by the notch.

6. An endodontic file comprising:
a handle and a bore having a closed top and a closed bottom, the bore formed entirely through the handle and being bound by an inner wall;
a fluted shank extending from handle along an axis, wherein the bore is aligned transverse to the axis;
a notch formed in communication with the bore, the notch extending into the bore between the closed top and closed bottom of the bore and comprising opposed, flat, and convergent first and second faces extending and converging inwardly into the handle and terminating at opposed, flat, and parallel upper and lower rear edges, respectively, at an inner end of the notch at the inner wall, wherein the notch is biased to move from an open condition to a closed condition;
the first and second faces are longer than the upper and lower rear edges;
the first face is oriented downward and inward at a first angle with respect to a line extending through the notch normal to the axis, the second face is oriented upward and inward at a second angle with respect to the line extending through the notch normal to the axis, and the second angle is greater than the first angle;
in the closed condition of the notch, the first and second faces are separated from each other, and the upper and lower rear edges are in flush and direct contact, so that the inner of the notch maintains continuity of the inner wall of the bore;
in the open condition of the notch, the first and second faces are separated from each other, and the upper and lower rear edges are separated from each other by a gap, so that the inner end is a discontinuity in the inner wall of the bore; and
during movement of the notch between the open and closed conditions, the first and second faces move toward and apart from each other in a direction aligned with the axis.

7. The endodontic file of claim 6, wherein the notch defines an entrance to the bore only in a direction transverse to the axis.

8. The endodontic file of claim 6, wherein the bore has a cylindrical shape.

9. The endodontic file of claim 6, wherein the first and second faces are asymmetric with respect to the line extending normal to the axis.

10. An endodontic file comprising:
a handle and a bore formed entirely through the handle;
a fluted shank extending from the handle along an axis;
a notch formed in communication with the bore and extending through the handle to the bore in a direction which is lateral to the axis;
the bore is bounded by an inner wall with a continuous cylindrical shape and is aligned transverse to the axis; and
the notch has an inner end terminating at the inner wall, and opposed, flat, and convergent first and second faces extending inwardly into the handle and terminating at opposed, flat, and parallel upper and lower rear edges at the inner end, wherein the notch is biased to move from an open condition to a closed condition;
the first and second faces are longer than the upper and lower rear edges;
the first face is oriented downward and inward at a first angle with respect to a line extending through the notch normal to the axis, the second face is oriented upward and inward at a second angle with respect to the line extending through the notch normal to the axis, and the second angle is greater than the first angle;
in the closed condition of the notch, the first and second faces are separated from each other, and the upper and lower rear edges are in flush and direct contact, so that the inner end of the notch maintains the continuous cylindrical shape of the inner wall;
in the closed condition of the notch, the first and second faces are separated from each other, and the upper and lower rear edges are separated from each other by a gap, so that the inner end is a discontinuity in the inner wall of the bore; and
during movement of the notch between the open and closed conditions, the first and second faces move toward and apart from each other in a direction aligned with the axis.

11. The endodontic file of claim 10, wherein the notch defines an entrance to the bore only in a direction transverse to the axis.

12. The endodontic file of claim 10, wherein the notch is configured to open only in a direction parallel with respect to the axis.

13. The endodontic file of claim 10, wherein the first and second faces are asymmetric with respect to the line extending normal to the axis.

14. The endodontic file of claim 10, wherein the bore has a closed top unbroken by the notch.

* * * * *